Figure 1:
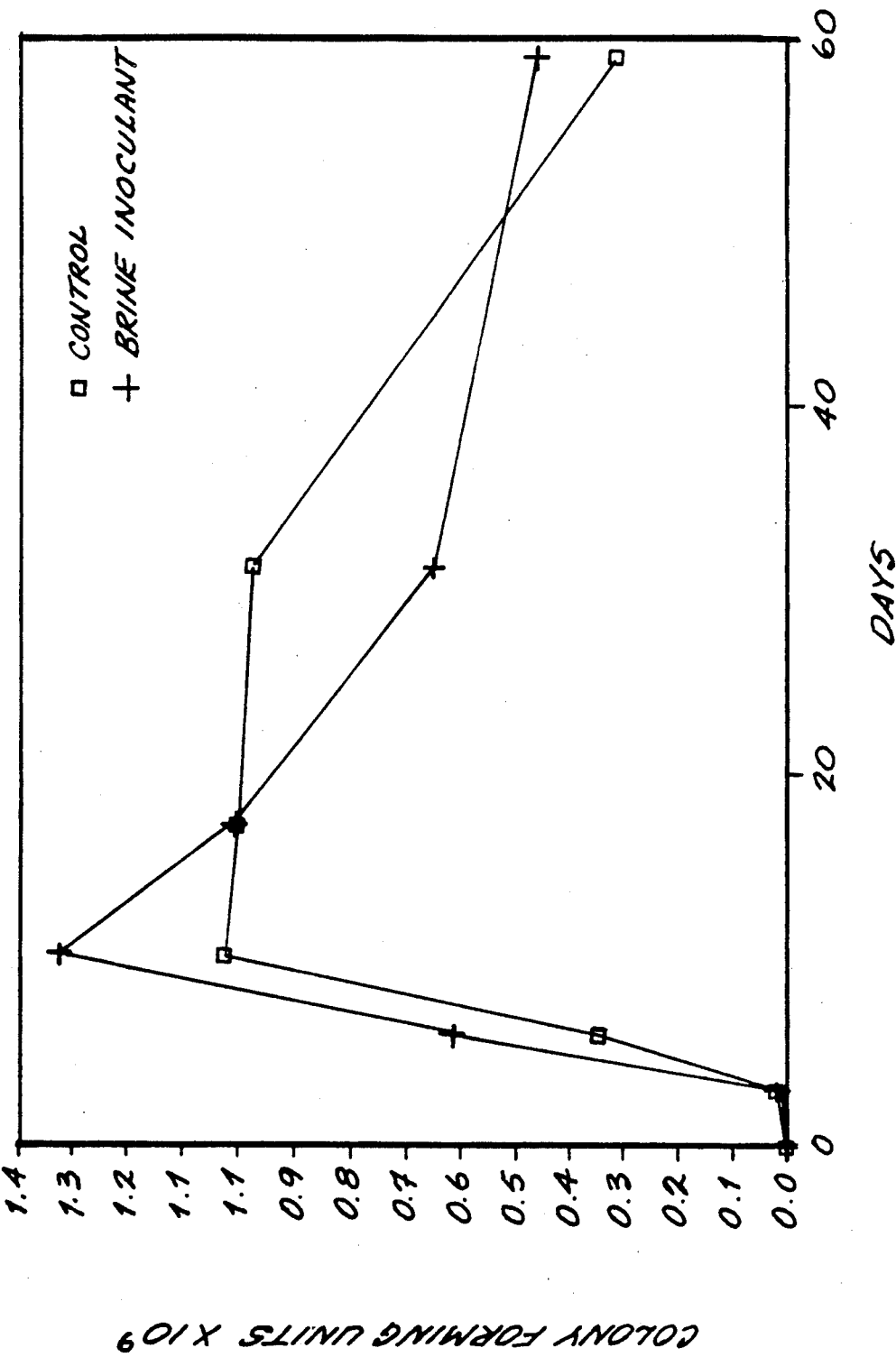

United States Patent [19]

Grant

[11] Patent Number: 5,002,778

[45] Date of Patent: Mar. 26, 1991

[54] MICROBIAL PRODUCT AND PROCESS FOR PRODUCING SAME FROM VEGETABLE BRINE

[75] Inventor: Michael A. Grant, Tacoma, Wash.

[73] Assignee: Curtice-Burns, Inc., Rochester, N.Y.

[21] Appl. No.: 425,509

[22] Filed: Oct. 19, 1989

Related U.S. Application Data

[63] Continuation of Ser. No. 152,930, Feb. 5, 1988, abandoned.

[51] Int. Cl.$^5$ .............................................. A23K 3/00
[52] U.S. Cl. ...................................... 426/53; 426/54; 426/623; 426/636; 426/807
[58] Field of Search .............................. 426/53, 54, 49

[56] References Cited

U.S. PATENT DOCUMENTS

| | | | |
|---|---|---|---|
| 2,546,101 | 3/1951 | Kalis | 426/54 |
| 2,733,146 | 1/1956 | Holst | 426/54 |
| 3,677,897 | 7/1972 | Jeffreys | 426/49 |
| 3,920,858 | 11/1975 | Morris | 426/54 |

OTHER PUBLICATIONS

Desrosier et al., "The Technology of Food Preservation", Fourth Edition, 1982, Avi Publishing Co., Westport, Conn., pp. 344–351.

Palnitkar et al., "Recycling Spent Brines in Cucumber Fermentations", J of Food Science, vol. 40 (1975), pp. 1311–1315.

Primary Examiner—R. B. Penland
Attorney, Agent, or Firm—Christensen, O'Connor, Johnson & Kindness

[57] ABSTRACT

A process for producing silage from fermentable forage chop is provided. The process consists of first preparing a microbial product by incubating fermentable vegetable matter in a brine and isolating the microbial product from the brine. The forage chop is then inoculated with the microbial product at a rate of from $10^2$–$10^7$ colony-forming units/g forage chop. The microbial product is characterized, and an improved pickling tank producing the microbial product is described.

6 Claims, 3 Drawing Sheets

MICROBIAL PRODUCT AND PROCESS FOR PRODUCING SAME FROM VEGETABLE BRINE

This application is a continuation application based on prior copending application Ser. No. 07/152,930, filed on Feb. 5, 1988, now abandoned.

TECHNICAL FIELD

This invention relates to microbial products and the process for their production. The microbial products of this invention are produced from the brines of fermentable vegetable matter. More particularly, the microbial products of this invention are used as silage inoculants.

BACKGROUND OF THE INVENTION

Fermenting and storing forage plants in an enclosed space or silo is an important way of providing fodder for domestic animals. However, natural fermentation is not always successful. This is thought to be due to the fact that the most important bacteria necessary for successful fermentation, i.e., Lactobacillus, Pediococcus, and Leuconostoc, are very scarce on the living undamaged plant tissue to produce silage. To improve the reliability of successful fermentation of forage plants, various silage additives have been proposed. Many of these additives, either alone or in combination, have been shown not only to enhance forage fermentation and reduce storage losses but to increase the food value of the forage plants. A review of various additives and their effect on silage can be found in *The Biochemistry of Silage*, Peter McDonald, pp. 129-67, John Wiley and sons (1981).

When used as silage inoculants, the various additives are referred to as "stimulants" and exert their effect by encouraging rapid lactic acid fermentation. One of the ways in which forage lactic acid fermentation can be stimulated is by the addition of microorganisms that increase the population of lactic acid-producing bacteria. The characteristics of ideal microbiological stimulants have been defined by Whittenbury (1961) Ph.D. thesis, University of Edinburgh, and include organisms that provide the maximum amount of lactic acid from sugars immediately available, grow vigorously and dominate other organisms, are acid tolerant to at least pH 4.0, are capable of fermenting sucrose, glucose, fructose, and pentose, are homofermentative (producing only lactic acid), do not decompose organic acids, possess a growth temperature range exceeding 50° C., and possess little or no protolytic activity. Based on these criteria, Whittenbury suggested the pediococci and homofermentative lactobacilli would be the most suitable microorganism.

Pure cultures of *Lactobacillus plantarum* have been studied as silage inoculants and evaluated based on the Whittenbury criteria. Inoculation with *L. plantarum* of alfalfa, corn, sorghum, and wheat silages was reported by Ely, et al., *J. Dairy Sci.* 64:2378-2387 (1981). These authors reported that in small test silos, total facultative anaerobic microflora were increased in all silages by the addition of *L. plantarum*, and that the total numbers of lactobacilli were increased, above that of controls, in all but corn silages. In comparable studies, addition of *L. acidophilus* had no positive effect on the inoculated silages, demonstrating that the particular inoculant species is critically important. Rooke, J.A., *Animal Feed Sci. and Tech.*, 13:269-279 (1985) reported similar results for silage inoculants containing *L. plantarum* added to perennial ryegrass. These results were in contradiction to those reported by McDonald (1981), leading Rooke, et al. to propose that different strains of *L. plantarum* may produce different results.

Moon, et al., U.S. Pat. No. 4,528,199, have disclosed a unique strain of lactobacillus, namely *L. plantarum* 2B, isolated from a corn silage fermentation that had not been inoculated with any supplemental bacteria. Inoculation of various forage materials with this strain were reported to produce superior results over a wide temperature range for all forages tested. The tests reported by Moon, et al.; Ely, et al.; and others were, however, conducted in experimental silos, where conditions were carefully controlled. These authors acknowledge that experience under normal farm conditions, where temperature and degree of anerobises are neither uniform nor carefully controlled, can produce results significantly different from those reported above.

Another problem with using a pure strain of *L. plantarum* as an inoculant is that this species has a relatively narrow pH growth curve and does not begin to produce lactic acid until the pH reaches about 5.0. For this reason, McDonald has suggested that the ideal inoculum should contain, in addition to *L. plantarum*, another species of bacteria that is active in the pH range of from 6.5 to 5.0, such as *Streptococcus faecalis*. Inoculation with a combination of these two bacteria resulted in a well preserved silage having a final pH of 4.1, with *S. faecalis* dominating during early stages of fermentation, finally giving way to the acid tolerant *L. plantarum* when the pH fell below 5.0.

An alternative solution to the problem is disclosed by Brown et al., U.S. Pat. No. 3,147,121. These inventors disclosed the use of *Pediococcus pentosaceus* (formerly *cerevisiae*) as a silage inoculant because this species produces lactate over a broad pH range. Inoculation of forage material with this bacteria produced satisfactory results in experimental test silos, but no data is provided under actual farm conditions.

Several authors have suggested a mixed culture of bacteria is preferable for use as a silage inoculant. A mixed culture of *S. faecalis, L. plantarum* and *Leuconostoc mesenteroides* has been demonstrated to be effective for inoculating ryegrass and clover (McDonald (1981)). Others have suggested that the safest approach for finding effective cultures is to isolate them from silage produced from the plants and under the conditions expected to occur where the inoculum is used, Lesins, et al., *Can. J. Animal Sci.* 48:15-25 (1968). Unfortunately, this solution to produce the best inoculation medium is not always possible. Furthermore, it is not clear that the best inoculant is one containing only the species that finally dominates the silage.

From the foregoing description of the prior art, it will be appreciated that a useful silage inoculant is needed, one that can effectively ensile a wide variety of forage material under the quite variable conditions found in farm silos. The inoculant should foster a timely succession of nonpathogenic microflora, culminating in dominating homofermentative lactate-producing organisms that are capable of quickly lowering the pH of the fermentable forage material to a pH suitable for preservation.

SUMMARY OF THE INVENTION

The invention consists of a process for producing silage from fermentable forage chop suitable for use as animal fodder comprising incubating a brine containing vegetable matter to form a fermentative microbial product in the brine, isolating the brine containing the microbial product from the vegetable matter, and inoculating the forage chop with the microbial product. The concentration of salt in the brine ranges from about 2% to about 19% by weight, and it is preferred that the brine be incubated at a temperature of from 15° C. to 30° C. for from about 5 to about 20 days. The vegetable matter incubated in the brine typically consists of cucumbers, olives, or cabbage. Normally the microbial product is first removed from the brine prior to use. The removing step usually consists of either centrifugation or filtration.

The inoculating step consists of adding to the forage chop an aqueous suspension of the microbial product produced as described above, in an amount effective to lower the pH of the forage to a level that will not support the growth of Clostridium botulinum or Listeria monocytogenes or other undesirable microorganisms, and will minimize the amount of nutrients lost from the forage prior to its consumption. The method is suitable for use with forage chop selected from the group consisting of corn, ryegrass, sedge, wheat, alfalfa, sorghum, oats, grass, and clover. The method usually requires the addition of from about $1 \times 10^2$ colony-forming units (CFU)/g forage chop to about $1 \times 10^7$ CFU/g forage chop. It is preferred that at least $1 \times 10^4$ CFU/g forage chop be added to ensure effective ensiling.

The invention also consists of the isolated microbial product produced by the method described above. This microbial product is preferably used in a kit for ensiling forage chop by the process described above.

The invention includes an improved pickling tank having means for separating the microbial product from the brine. The method of separation consists of centrifugation.

BRIEF DESCRIPTION OF THE DRAWINGS

The following figures demonstrate the effectiveness of the microbial product of the present invention as a silage inoculant.

FIG. 1 is a graph of silage pH for chopped corn silage versus time.

FIG. 2 is a graph of the number of lactic acid bacteria colony-forming units in chopped corn silage versus time.

FIG. 3 is a schematic view of an improved pickling tank.

DETAILED DESCRIPTION OF THE INVENTION

A microbial product produced by incubating vegetable matter in brine can be used as silage inoculant for a wide variety of forage chop. The microbial product is useful for producing silage from fermentable forage chop for use as animal fodder. Forage chop used herein means any fermentable vegetable matter suitable for consumption by domestic animals, especially ruminants. Examples of suitable fermentable vegetable matter include, but are not limited to: corn, ryegrass, orchard grass, sedge, wheat, alfalfa, sorghum, oats, grasses, and clover.

PREPARATION OF THE SILAGE INOCULANT

The brining of vegetables and subsequent natural fermentation is a process that originated before recorded history. The general procedures are well known to those in the art. These procedures are described in Fleming, H.P. *Economic Microbiology* 7 pp. 227–258, Academic Press, Inc., New York (1982), herein incorporated by reference. Almost any vegetable matter is suitable for use in producing the silage inoculant of the present invention. Preferred vegetables include: cabbage, olives, cucumbers, carrots, green beans, lima beans, green peas, corn, okra, green tomatoes, cauliflower, whole peppers, pepper mash, onions, citrons, beets, turnips, radishes, chard, brussels sprouts, mustard leaves, lettuce, fresh peas, vegetable or fruit processing waste, and combinations thereof. However, the most preferred vegetables are cabbage, olives, and cucumbers.

the vegetables are treated in a variety of ways before brining, depending on their nature. The predominant microorganisms and consequent utility as a silage inoculant varies somewhat with the exact type of vegetable fermentation process. For example, cabbage used for sauerkraut is washed, wilted, cored, trimmed, and shredded prior to brining. The prebrining treatment of other vegetables is disclosed in Fleming (1982) and references cited therein.

Vegetables are brined at various salt concentrations, depending on the particular vegetable. The preferred brining range is from about 2% to about 19% w/v salt. The preferred salt concentration in the brining solution is about 2–3% w/v for cabbage, 5–8% w/v for cucumbers, and 4–7% w/v for green olives.

In general, vegetables and brining solution are added to large fermentation tanks and headed with timbers to keep the vegetables submerged. Additional brining solution is then added to cover the vegetables and heading timbers. The surface of the brining solution is typically left exposed to sunlight to prevent the buildup of surface mold.

Although the vegetables are usually washed after harvesting and may be subjected to various prebrining treatments, ample indigenous epiphytic microorganisms remain to provide a natural inoculum once they are placed in the brine. Occasionally, commercial inoculants consisting of viable lactic acid bacteria are added to ensure successful pickle fermentation, but this is neither a crucial nor a widespread practice. Upon brining, many types of microorganisms begin to grow using the fermentable sugars in the vegetables as nutrient sources. The varieties of microorganisms are initially restricted by their tolerance to the saline conditions of the brine. A natural succession of microorganisms then proceeds in the brine, directed by the changing environment produced by respiring plant tissue and by-products of bacterial metabolism. Ultimately, large amounts of lactic acid are released into the brine by various species of lactate producing bacteria, resulting in a reduction in pH that soon prevents the growth of any microbes except aciduric bacteria and yeasts. Potential pathogens are inhibited by the combination of low pH, elevated NaCl concentration, and substantial anaerobiosis. Lactic acid bacteria predominate and their population increases in a fashion typical of the standard bacterial growth curve. During this process, lactic acid is the main end-product formed as the fermentable carbohydrates are catabolized. The rate of growth is a function of the ambient temperature, since the fermentation tanks are usually not temperature controlled. In a typical late-summer fermentation, the majority of the carbohydrate will have been consumed after 7 to 9 days in northern states and the lactic acid bacterial population will level off. In warmer climates, the carbohydrate consumption and bacterial growth will be accelerated. In cucumber pickling, for example, this cessation of growth usually occurs when the total population of lactic bacteria is about 100,000,000–500,000,000 per ml. This leveling off of the bacterial population is referred to as "stationary phase." For reasons not fully understood, the lactic bacterial population begins to decline relatively rapidly once stationary phase is reached.

Once the fermentable sugars are depleted from the vegetable matter, and the lactic acid bacterial population has reached stationary phase, the bacteria are harvested. Harvesting the bacteria may be conducted by any standard procedure; however, filtration and centrifugation are preferred. The most preferred separation method is to centrifuge the brine with a continuous flow separator. An example of a satisfactory separator is a WESTFALIA separator, Model SA 7-06-076. Brine containing the microbial product is removed from the tank through a conduit and passed through the separator, where the microbial product is removed. The brine, containing salt and organic acids, is preferably returned to the tank through a second conduit, thereby maintaining the salt and organic acid concentration in the fermentation tank. The brine is essential in stabilizing the fermented vegetable matter, and the presence of the microbial product is not essential once the stationary phase is reached.

The microbial product isolated from the separator can be used as isolated or frozen in polyethylene bottles for later use; however, it is preferred that the microbial product be first mixed with a cryogenic protecting agent, such as glycerol, to minimize microbial destruction caused by freezing and thawing. Freeze-drying the microbial product is an equivalent procedure.

The microbial product so produced and isolated comprises the silage inoculant of the present invention. This silage inoculant contains a large number of bacterial and yeast genera, species, and varieties. Yeast typically comprise less than 1% of the total microbial population. Yeast have been intentionally added to determine whether they would enhance the ensiling process (N. J. Moon, L. O. Ely, E. M. Sudweeks, 1981, Fermentation of Wheat, Corn, and Alfalfa Silages Inoculated with *Lactobacillus acidophilus* and Candida sp. at Ensiling. *J. Dairy Sci.* 64:807–813). Fermentative yeast predominate in anoxic vegetable fermentation brines, where they carry out secondary fermentation, which may enhance total production of acid since fermentative yeast are able to ferment residual sugars (in vegetable matter) after the pH has reached a level inhibitory to lactic acid bacteria. On the other hand, excessive populations of fermentative yeast early in the ensiling process could compete with lactic acid bacteria for fermentable carbohydrate and large populations of oxidative yeast may cause aerobic deterioration problems when silage is fed out. Yeast populations of less than 1% present in vegetable brine had no impact on the overall numbers of yeast that normally develop in silage. In an experiment with grass-legume silage, there was no significant difference ($p < 0.05$) in the total yeast population of control silage and silage inoculated with cell concentrate from a pickle tank. The same result was observed in a separate experiment with corn silage.

The microbial product is assayed by standard assay procedures to determine the number of colony-forming units (CFU) per ml (especially the number of lactic acid bacteria) and packaged for use with instructions to dilute the product so that it can be easily added in an amount effective to lower the pH of forage chop to a level that will not support the growth of *Clostridium botulinum* or *Listeria monocytogenes* or other microbial species that might reduce the feed value of the chop. This amount is usually about $1 \times 10^4 - 1 \times 10^5$ CFU/g of forage chop. It will be appreciated by those skilled in the art that a large number of additives can be included in the silage inoculant of the present invention, such as enzymes, sugars, organic acids, aldehydes, and reducing agents, to further enhance the fermentation process. Many of these additives are discussed in McDonald (1981).

As previously stated, the microbial product produced by the procedure described above contains a large number of strains, species, and genera of both microorganisms. Their complete identification is unknown; however, the laws of microbiology governing brined vegetable fermentation mandate that certain types of lactic acid bacteria predominate. In sauerkraut fermentation, the natural succession of bacteria is known to proceed in the following order: *Streptococcus faecalis; Leuconostoc mesenteroides; Lactobacillus brevis; Pediococcus pentosaceus;* and finally *Lactobacillus plantarum*, while in cabbage and cucumber fermentation, only the latter four species dominate (Fleming 1982). Accordingly, the bacterial component of the instant silage inoculant consists essentially of the above-enumerated species and is particularly enriched in *L. plantarum*. Even though *L. plantarum* finally dominates the culture, substantial numbers of the other described species as well as unidentified species are represented. Furthermore, unlike silage inoculants produced from pure cultures, the instant inoculant contains a large number of varieties of *L. plantarum*.

Additionally, the silage inoculant of the present invention contains smaller amounts of yeast. The principal fermentative yeasts of this invention comprise: Torulopsis sp., Hansenula sp., and Saccharomyses sp. Other fermentative and oxidative yeasts also are present, the exact composition depending upon the nature of the vegetable chop, salinity, and pH of the brine at harvest time, as well as other factors.

METHOD OF INOCULATION

The instant invention does not alter the normal ensiling process known to those skilled in the art, except that the inoculant comprises a wide variety of genera, species, and varieties of both aciduric microorganisms. The advantage of ensiling with an inoculant containing a wide variety of microflora is that it substantially improves the probability that proper fermentation and preservation of a wide variety of silage chop under actual farm conditions will occur. The instant inoculant does not require the addition of any additives of the type described by McDonald (1981) to produce a successful fermentation. Nevertheless, under certain conditions, additives of the type described above may be included in the inoculant to enhance fermentation of the forage chop. Accordingly, the method of the present invention consists of producing silage from fermentable forage chop suitable for use as animal fodder, comprising inoculating the forage chop with the microbial product produced as described above, in an amount effective to lower the pH to a level that will not support the growth of pathogenic organisms such as *Clostridium botulinum* or *Listeria monocytogenes* and will preserve the maximum amount of nutrients for later consumption by farm animals.

These pathogens do not grow below about pH 4.8–4.6. Therefore, the amount of microbial product necessary to ensure proper fermentation and preservation of the forage chop will be that amount sufficient to lower the pH to 4.6 within about 40 days and preferably within 15 days. This amount is readily determined by those skilled in the art and varies with the type of forage chop ensiled. Typically, the amount ranges from about $1 \times 10^2$ to $1 \times 10^7$ CFU/g silage chop. It is preferred, however, that at least $1 \times 10^4$ CFU/g forage chop be applied to ensure proper fermentation and preservation.

After ensiling with the silage inoculant of the present invention, fermentation proceeds rapidly and primarily via the homofermentative pathway. This is due to the large number of homofermentative lactobacilli present in the inoculant. The total number of lactobacilli increases rapidly during the first 10 days after inoculation. FIG. 1 compares the number of lactobacilli produced in a grass-legume forage chop after inoculation with $45 \times 10^6$ CFU/lb forage chop versus a non-inoculated control. During the critical first 10-day period, lactobacilli dominate the culture much more rapidly in the inoculated sample than in the control. Assays of the inoculated silage after the first 7 days indicate that more than 90% of the lactobacilli present are the homofermentative $L.$ $plantarum$. It is known in the art that metabolism via the homofermentative pathway produces a superior silage when compared to heterofermentation.

Figure 2:
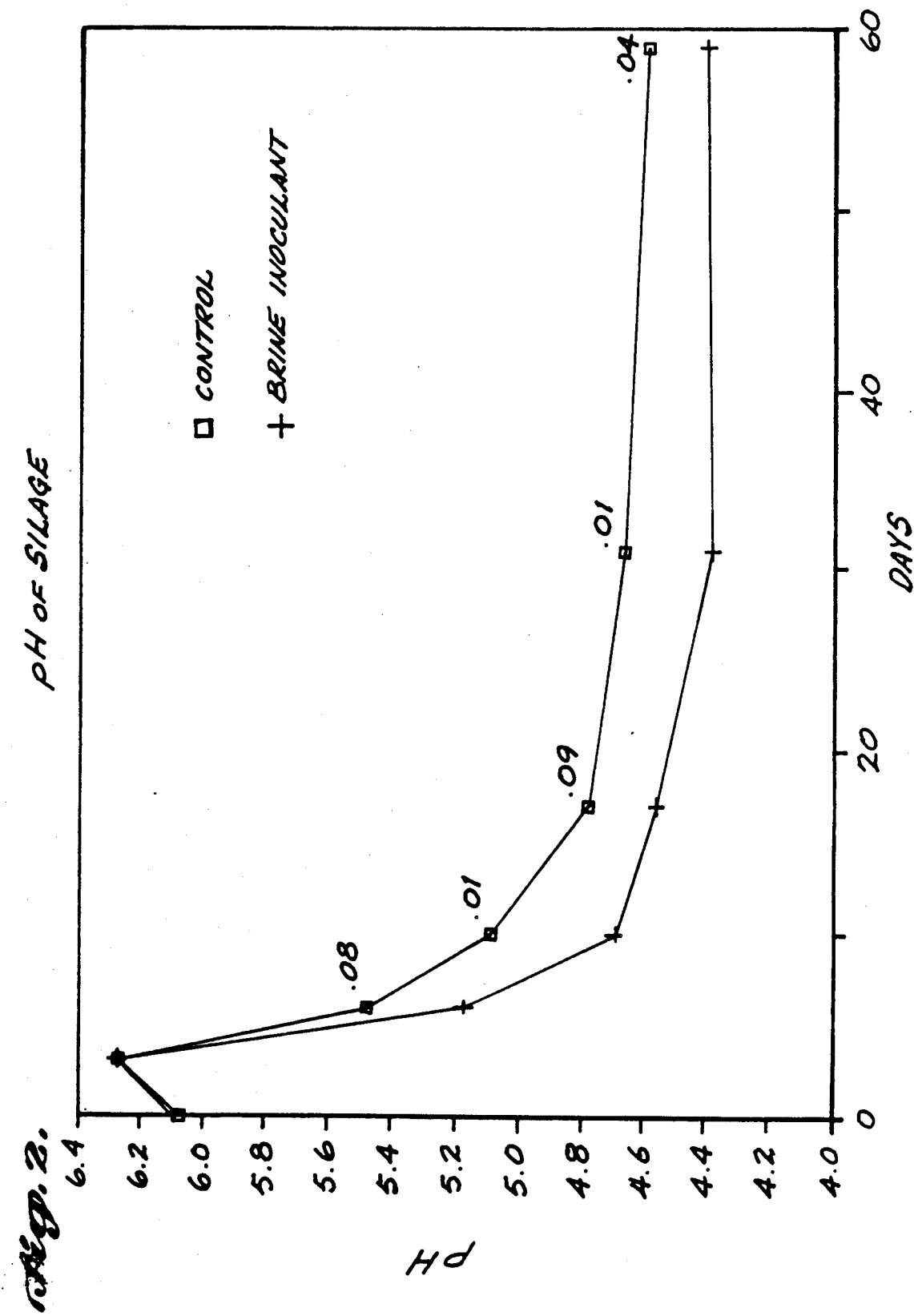

It is also known in the art that the more rapidly the pH of the fermenting forage chop is lowered, the more unlikely that undesirable mold, heterofermentative bacteria, and pathogenic bacteria will develop. FIG. 2 compares the pH of a grass-legume forage chop after inoculation with $45 \times 10^6$ CFU/lb forage chop versus a non-inoculated control. During the first 10 to 15 days, the pH of the fermenting forage chop drops to a level that will not support the growth of pathogenic bacteria such as $C.$ $botulinum$ or $L.$ $monocytogenes$, while in the control more than 40 days are required before the pH drops to a level that prohibits growth of these undesirable microorganisms. Upon reaching pH 4.6, the silage produced as described above remains substantially stable to decay, provided it is maintained under anaerobic conditions.

IMPROVED PICKLING TANK

Figure 3:
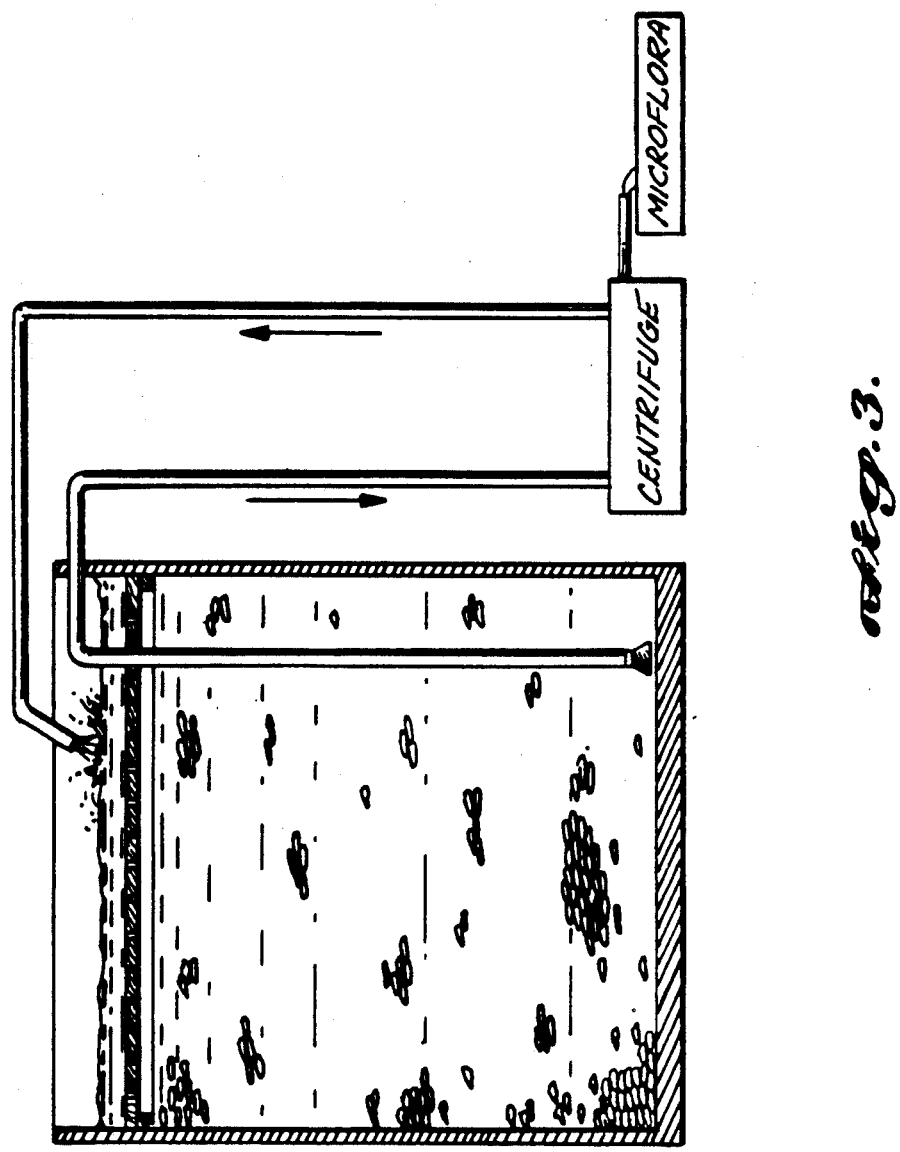

The improved pickling tank of the present invention is schematically represented in FIG. 3 and consists of a standard pickling tank adapted to accept a separator or centrifuge and associated incurrent and excurrent conduit. Pickling tank, as used herein, means any large tank or vat suitable for use in fermenting vegetable matter such as cucumbers, cabbage, and olives. The separator or centrifuge may be any separator; however, it is preferred that it be a continuous flow separator, such as a WESTFALIA Model SA 7-06-076. Employing a continuous flow separator allows brine containing microflora to be removed from the pickling tank through the excurrent conduit; centrifuged, substantially removing microflora from the brine; and returned to the tank through the incurrent conduit in a continuous operation. The opening of the excurrent conduit into the pickling tank is located below the heading boards and preferably near the bottom of the tank. It is most preferred that this opening be located between 1 to 3 feet of the bottom of the tank and be equipped with a screening mechanism to prevent loss of vegetable matter through the excurrent conduit. The opening of the incurrent conduit into the pickling tank may be located at any level, but is preferred that it be located above the heading boards. The diameter of either the incurrent or excurrent conduit may be of any size, limited only by the intake and output capacity of the separator. The separator is preferably employed to remove microflora during the time when the water soluble carbohydrate concentration is running out and the bacteria are reaching stationary phase. Preferably, this procedure is employed during the 5th through the 10th day after brine has been added to the vegetable matter, and most preferably during the 7th through the 9th day. In warmer climates, these time periods would be reduced to correspond to the earlier stationary phase of microbial growth. The brine that is returned to the pickling tank may still contain some microflora, preferably less than $10^7$ CFU/ml and most preferably less than $10^6$ CFU/ml.

Vegetable matter fermented in the improved pickle tank of the present invention have better flavor and texture. It is believed this is due, at least in part, to the fact that the brine derived from the pickling tank and used as the packing liquor contains substantially fewer of the microflora responsible for spoilage. Accordingly, both the temperature and duration of pasteurization may be reduced, resulting in enhanced flavor and texture of the pickled vegetables.

Another advantage of the instant improved pickle tank is the reduced cost of operation. Vegetable brine that has a lower biological and chemical oxygen demand can be disposed of at a lower cost. By removing the microflora from the brine prior to disposal, substantial savings in the production cost of fermented vegetables can thus be realized.

Additionally, the cell concentrate collected from the brine can be introduced into tanks of newly brined vegetables rather than sold as a silage inoculant. This increases the speed of fermentation and curing, thereby allowing the product to be marketed more rapidly. Furthermore, inoculation of fresh tanks with the microbial concentrate, with its preponderance of $L.$ $plantarum$, should result in a better flavored pickled vegetable. Aurand ($J.$ $Food$ $Sci.$ 30:288, 1965) showed that cucumbers inoculated with $L.$ $plantarum$ had a clean flavor, while $L.$ $brevis$ and $P.$ $pentosaceus$ fermentations caused somewhat bitter taste and slight off-odor.

The following examples are illustrative of methods useful for practicing the present invention and are not intended in any way to limit the scope of the invention.

EXAMPLE I

Formation of the Microbial Product

One gallon of brine was collected from a 1,000 gallon pickle tank. This was a standard open tank in which pickle fermentation had begun about one week earlier with no starter cultures added. Cucumbers, salt, and water had been added to the tank with a final salt concentration of 6%. This brine contained 120,000,000 viable lactics/ml at time of collection. Peak lactic population in the pickle tanks is typically 100,000,000 to 500,000,000 per ml. The brine was centrifuged using a Jouan refrigerated centrifuge at 3850 rpm for 10 minute runs and an IEC model UV centrifuge at 1900 rpm for 20 minute runs. This resulted in 69 ml of cell paste containing 1,500,000,000 lactics/ml.

EXAMPLE II

Ensiling

The 69 ml of cell paste from Example I were removed from refrigeration and gently warmed to room temperature. A chopped grass-legume mixture was used for the experiment and the control. For the control, approximately 3 liters of water was hand-sprinkled over 120 kg of fodder. Four-kilogram aliquots of this material were placed in 5-gallon pails, which were double lined with plastic bags. The bags were knotted and pails incubated in a barn. For the inoculated material, the 69 ml of cell paste were diluted in approximately 1 liter of saline, and this was hand-sprinkled over approximately 50 kg of fodder. Four kg aliquots were placed in pails for controls. The number of viable lactics added to the fodder was found to be approximately 45,400,000 per pound of silage. Silage from both the inoculated and control samples were assayed periodically. At day 10, $1.35 \times 10^9$ CFU/ml were observed in the inoculated sample with a pH of 4.65, compared to $0.98 \times 10^9$ CFU/ml and pH 5.10 in the control.

EXAMPLE III

Ensiling

Natural fermentation proceeded in a tank of brined cucumbers at an ambient temperature of 60°-75° F. for six days. A WESTFALIA Model SA 7-06-076 automatic centrifuge set at an operating pressure of 80 PSI and flow rate of 100 gallons per hour was then used to concentrate lactic acid bacteria in the brine. The brine contained $1.14 \times 10^8$ CFU/ml. After passage through the centrifuge, the effluent contained $2.9 \times 10^5$ CFU/ml, indicating that approximately 99.7% of the cells were removed from the brine passed through the centrifuge. Approximately 17 gallons of concentrate were collected with a viable lactic acid bacteria count of $1.84 \times 10^{10}$ CFU/ml.

A portion of the concentrate was used to inoculate 200 lb of grass-legume forage at a level of $1 \times 10^5$ viable lactic bacteria per gram. Lactic treated and control forage was packed in double plastic lined pails and incubated as in Example II. Pails were opened on days 2, 5, 9, 20, and 62 for microbiological and chemical analysis. Lactic bacterial populations were determined by diluting 50 gm portions of silage in 450 ml volumes of sterile saline and agitating 3 minutes in a Stomacher Model 3500 laboratory blender to suspend epiphytic microorganisms on plant tissue. Decimal dilutions in saline were then prepared in saline according to standard procedures (e.g., F.D.A. Bacteriological Analytical Manual, 6th edition, 1984, published by Association of Official Analytical Chemists) and aliquots used to prepare pour plates in Rogosa agar. Petri plates were incubated at 30° C. for 3 days before colonies were counted and used to calculate the viable lactic acid bacterial count.

On days 2, 5, 9, and 20, the population of lactic bacteria in the treated fodder was $1.11 \times 10^9$, $2.22 \times 10^9$, $1.81 \times 10^{109}$, and $1.35 \times 10^9$ CFU/g respectively. In contrast, the control populations on equivalent days were $7.80 \times 10^8$, $1.34 \times 10^9$, $1.03 \times 10^9$, and $8.50 \times 10^8$ CFU/g. The value of adding a silage inoculant was also demonstrated by pH values. On days 2, 5, 9, and 20, treated silage pH values were 5.60, 4.80, 4.48, and 4.31, whereas control values were 6.21, 5.49, 4.83, and 4.51.

While the invention has been described in conjunction with preferred embodiments, one of ordinary skill, after reading the foregoing specification, will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

The embodiments of the invention in which an exclusive property or privilege is claimed are defined as follows:

1. A process for producing silage from a fermentable forage chop suitable for use as animal fodder, comprising:
    incubating a brine containing vegetable matter selected from the group consisting of cucumbers, olives, and cabbage under the following conditions:
        concentration of salt in the brine: about 2% to about 19% by weight
        temperature: 15° to 30° C.
        time period: about 5 to about 20 days thereby forming a fermentative microbial product comprising a mixture of microorganisms indigenous to said vegetable matter in the brine;
    isolating the microbial product from the brine; and,
    inoculating said forage chop with an amount of the microbial product effective to result in a pH of about 4.6 to about 3.8 and to ensile said forage chop, wherein said forage chop is selected from the group consisting of corn, ryegrass, sedge, wheat, alfalfa, sorghum, oats, grass, and clover.

2. The process of claim 1, further comprising, after isolating the brine, removing the microbial product from the brine.

3. The process of claim 2, wherein the removing step comprises centrifugation.

4. The process of claim 2, wherein the removing step comprises filtration.

5. The process of claim 2, wherein the microbial product is added at a rate of at least $1 \times 10^2$ colony forming units per gram of forage chop.

6. The process of claim 2, wherein the microbial product is added at a rate of at least $1 \times 10^4$ colony-forming units per gram of forage chop.

* * * * *